(12) United States Patent
Shi et al.

(10) Patent No.: US 10,847,726 B2
(45) Date of Patent: Nov. 24, 2020

(54) IMIDIZO DERIVATIVES

(71) Applicants: Jianmin Shi, Rockville, MD (US); Eric W. Forsythe, Rockville, MD (US); David C. Morton, Columbia, MD (US)

(72) Inventors: Jianmin Shi, Rockville, MD (US); Eric W. Forsythe, Rockville, MD (US); David C. Morton, Columbia, MD (US)

(73) Assignee: The United States of America as represented by the Secretary of the ArmyWA (US)

( * ) Notice: Subject to any disclaimer, the term of this patent is extended or adjusted under 35 U.S.C. 154(b) by 150 days.

(21) Appl. No.: 16/120,825

(22) Filed: Sep. 4, 2018

(65) Prior Publication Data
US 2019/0131538 A1  May 2, 2019

Related U.S. Application Data

(62) Division of application No. 14/191,520, filed on Feb. 27, 2014, now abandoned.

(51) Int. Cl.
| | | |
|---|---|---|
| *H01L 51/50* | (2006.01) | |
| *C07D 519/00* | (2006.01) | |
| *H01L 51/00* | (2006.01) | |

(52) U.S. Cl.
CPC ........ *H01L 51/0067* (2013.01); *C07D 519/00* (2013.01); *H01L 51/0072* (2013.01); *H01L 51/5012* (2013.01); *H01L 51/5076* (2013.01); *Y02E 10/549* (2013.01)

(58) Field of Classification Search
CPC .................................................. H01L 51/0067
See application file for complete search history.

(56) References Cited

U.S. PATENT DOCUMENTS

| 5,766,779 A | 6/1998 | Shi |
|---|---|---|
| 7,985,974 B2 | 7/2011 | Nowatari et al. |
| 2002/0147339 A1 | 10/2002 | Batchelor |

FOREIGN PATENT DOCUMENTS

JP            2005044790 A    *    2/2005

OTHER PUBLICATIONS

JP2005044790, Machine Translation. (Year: 2005).*
Guckian et al., "Assessment of intercomponent interaction in phenylene bridged dinuclear ruthenium(II) and osmium(II) polypyridyl complexes," 2004, Dalton Trans., pp. 3943-3949. (Year: 2004).*
Tang, C. W., et al., "Organic Electroluminescent Diodes", Applied Physics Letters, vol. 51, Issue 12, Sep. 21, 1987, pp. 913-915.

* cited by examiner

*Primary Examiner* — Robert A Vetere
(74) *Attorney, Agent, or Firm* — Christos S. Kyriakou; Emily C. Moscati

(57) ABSTRACT

The present invention relates to imidizo derivatives containing a plurality of imidizo moieties linked by aryl or heteroaryl groups. The resultant imidizo derivates may advantageously be used in organic electronic devices, such as multi-layer organic electroluminescent devices or organic photovoltaic devices, and in chemical sensing applications as a host material.

31 Claims, 4 Drawing Sheets

IMIDIZO DERIVATIVES

CROSS-REFERENCE TO RELATED APPLICATIONS

This application is a divisional of and claims priority to U.S. patent application Ser. No. 14/191,520 titled "IMIDIZO DERIVATIVES" filed on Feb. 27, 2014, the entire contents of which are hereby incorporated by reference herein including all attachments and appendices which are also hereby incorporated herein by reference.

GOVERNMENT INTEREST

The embodiments described herein may be manufactured, used, imported and/or licensed by or for the United States Government without the payment of royalties thereon.

BACKGROUND

Technical Field

Embodiments of the present invention generally relate to organic materials and, more particularly, to imidizo derivatives containing a plurality of imidizo moieties linked by aryl or heteroaryl groups.

Description of Related Art

A wide variety of imidizo derivatives are used in the pharmaceutical industry as bioactive components in, for example, organic electroluminescent (EL) devices, as highly efficient emitting materials, electron injecting materials, and transport materials, and in surface coatings as UV-light absorbers. Additional derivatives providing improved functionality are continuously being sought.

Therefore, the inventors have provided improved imidizo derivatives containing a plurality of imidizo moieties linked by aryl or heteroaryl groups.

SUMMARY

Embodiments of the present invention relate to a compound having the following formula:

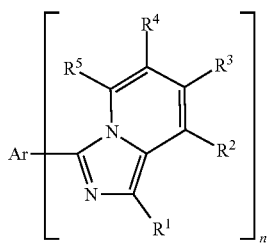

wherein, $R^1$, $R^2$, $R^3$, $R^4$, and $R^5$ are each independently a hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group; wherein n is an integer from 2 to 4; and wherein Ar is a linkage unit comprising aryl or heteroaryl or substituted aryl or heteroaryl groups.

In some embodiments, an imidizo compound is formed by the following scheme:

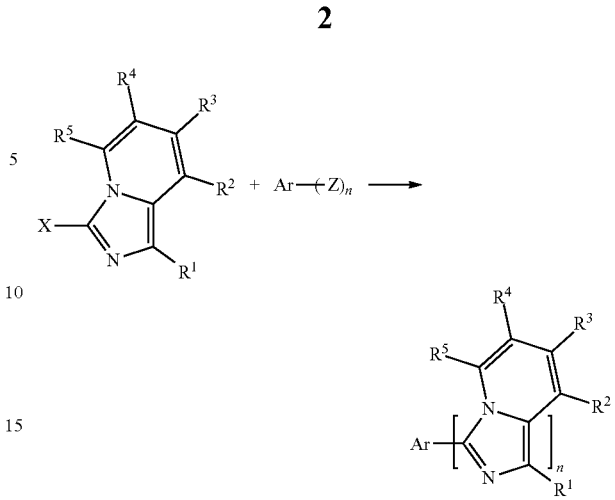

wherein, $R^1$, $R^2$, $R^3$, $R^4$, and $R^5$ are each independently hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group; wherein X is one of chloro, bromo, iodo, or cyano; wherein Ar is a linkage unit comprising aryl and heteroaryl groups or substituted aryl and heteroaryl groups; wherein Z is a reactive group; and wherein n is an integer from 2 to 4.

Other and further embodiments of the invention are described in more detail below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
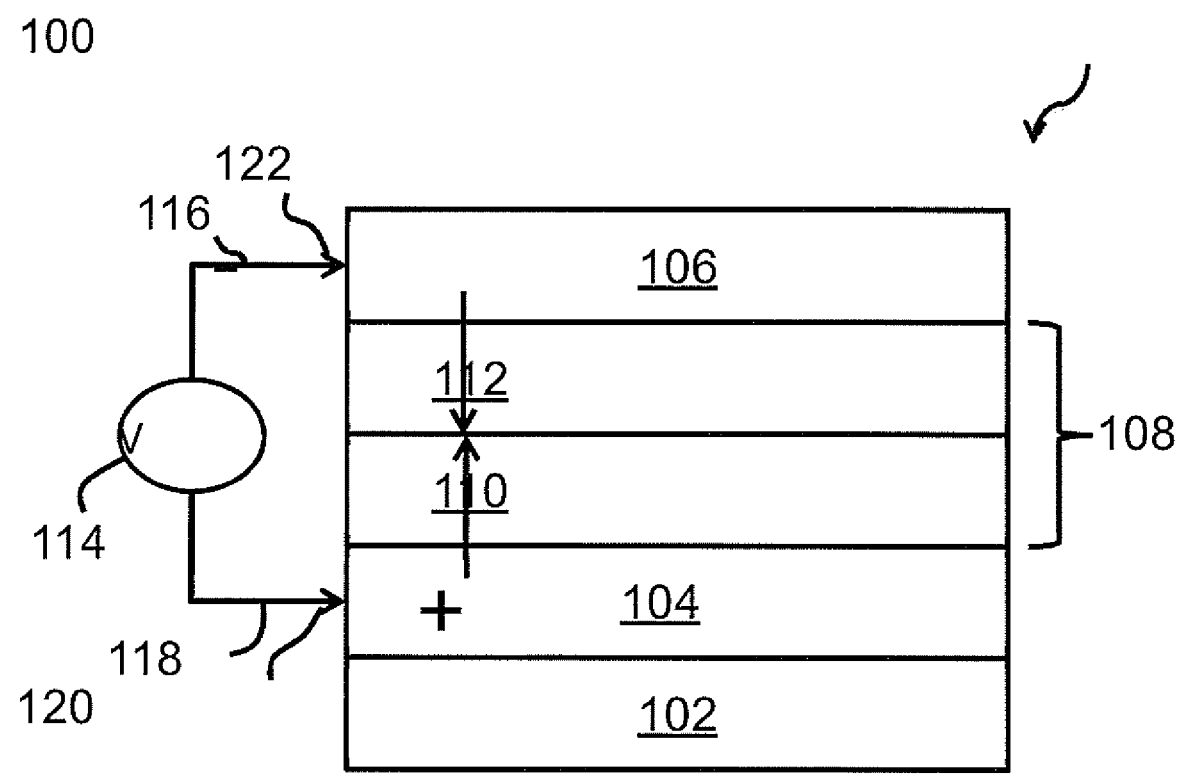
FIG. 1 depicts an organic electroluminescent device in accordance with some embodiments of the present invention.

Embodiments of the present invention include imidizo derivatives containing a plurality of imidizo moieties linked by aryl or heteroaryl groups. In some embodiments, the imidizo derivatives described herein may advantageously be used in organic electronic devices such as multi-layer organic electroluminescent (EL) devices or organic photovoltaic (OPV) devices or as a dopant in polymer organic EL or OPV devices. The imidizo derivatives may be used between two electrodes as emitting materials, electron injecting materials, and transport materials. In some embodiments, the imidizo derivatives described herein may advantageously be used as a host material in chemical sensing applications.

The following formula depicts an imidizo derivative in accordance with some embodiments of the present invention:

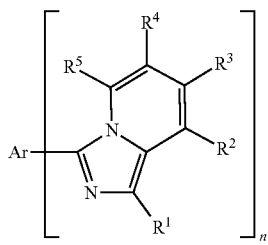

In some embodiments, $R^1$, $R^2$, $R^3$, $R^4$, and $R^5$ are each independently a hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group. In some embodiments, n is an integer from 2 to 4. In some embodiments, Ar is a linkage unit, for example a linkage unit that is an aryl or heteroaryl group or a substituted aryl or heteroaryl group.

In some embodiments, the alkyl or alkoxyl is a C1-C8 alkyl or alkoxyl. In some embodiments, the alkenyl or alkynyl is a C2-C8 alkenyl or alkynyl. In some embodiments, the aryl is a C6-C10 aryl. In some embodiments, the heteroaryl has 5 to 10 ring atoms and 1 to 3 ring hetero atoms. In some embodiments, the ring hetero atoms are nitrogen, sulfur, or oxygen. In some embodiments, the substitutions on the aryl or heteroaryl are independently a group, $R^6$, which is a hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group.

In some embodiments, the imidizo derivative described above is formed by the following scheme:

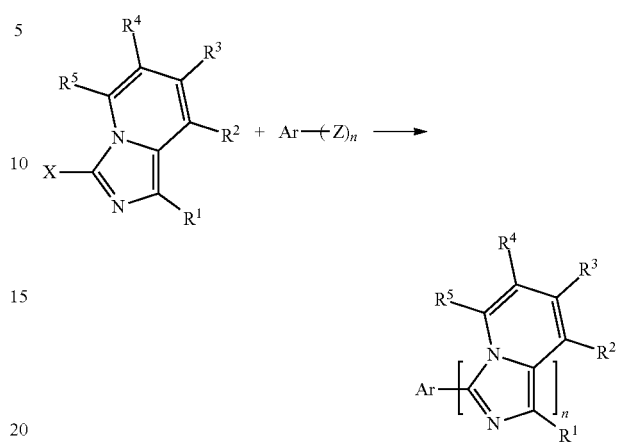

In some embodiments, as described above, $R^1$, $R^2$, $R^3$, $R^4$, and $R^5$ are each, independently hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group. In some embodiments, X is one of a chloro, bromo, iodo, or cyano group. In some embodiments, Ar is a linkage unit, for example a linkage unit that is an aryl or heteroaryl group or a substituted aryl or heteroaryl group. In some embodiments, Z is a reactive group, for example one of Li, MgCl. MgBr, $B(C_2H_4O_2)$, $B(C_2H_{12}O_2)$, or $B(OH)_2$. In some embodiments, Ar—Z is the product of Ar with a proton extracting reagent. In some embodiments, n is an integer from 2 to 4.

Representative examples of novel imidizo derivatives formed in accordance with some embodiments of the present invention include but are not limited to the following examples depicted in Table 1.

TABLE 1

Examples of novel imidizo derivatives

| Description | Imidizo Derivative Structure |
|---|---|
| Compound 1: 1,4-bis(3-phenylimidazo[1,5-a]pyridin-1-yl)benzene | |
| Compound 2: 1,4-bis(3-(pyridin-2-yl)imidazo[1,5-a]pyridin-1-yl)benzene | |

TABLE 1-continued

Examples of novel imidizo derivatives

| Description | Imidizo Derivative Structure |
| --- | --- |
| Compound 3: 1,4-bis(3-(pyrimidin-2-yl)imidazo[1,5-a]pyridin-1-yl)benzene | |
| Compound 4: 2,5-bis(3-phenylimidazo[1,5-a]pyridin-1-yl)pyrazine | |
| Compound 5: 2,5-bis(3-(pyridin-2-yl)imidazo[1,5-a]pyridin-1-yl)pyrazine | |
| Compound 6: 2,5-bis(3-(pyrimidin-2-yl)imidazo[1,5-a]pyridin-1-yl)pyrazine | |
| Compound 7: 1,3-bis(3-phenylimidazo[1,5-a]pyridine-1-yl)benzene | |
| Compound 8: 1,3-bis(3-(pyridin-2-yl)imidazo[1,5-a]pyridin-1-yl)benzene | |

TABLE 1-continued

Examples of novel imidizo derivatives

| Description | Imidizo Derivative Structure |
| --- | --- |
| Compound 9: 1,3-bis(3-(pyrimidin-2-yl)imidazo[1,5-a]pyridin-1-yl)benzene | |
| Compound 10: 2,5-bis(3-phenylimidazo[1,5-a]pyridin-1-yl)thiophene | |
| Compound 11: 2,5-bis(3-(pyridin-2-yl)imidazo[1,5-a]pyridin-1-yl)thiophene | |
| Compound 12: 2,5-bis(3-(pyrimidin-2-yl)imidazo[1,5-a]pyridin-1-yl)thiophene | |
| Compound 13: 2,5-bis(3-phenylimidazo[1,5-a]pyridin-1-yl)-1H-pyrrole | |
| Compound 14: 2,5-bis(3-(pyridin-2-yl)imidazo[1,5-a]pyridin-1-yl)-1H-pyrrole | |

TABLE 1-continued

Examples of novel imidizo derivatives

| Description | Imidizo Derivative Structure |
| --- | --- |
| Compound 15: 2,5-bis(3-(pyrimidin-2-yl)imidazo[1,5-a]pyridin-1-yl)-1H-pyrrole | |
| Compound 16: 1,1'-(1-ethyl-1H-pyrrole-2,5-diyl)bis(3-phenylimidazo[1,5-a]pyridine) | |
| Compound 17: 1,1'-(1-phenyl-1H-pyrrole-2,5-diyl)bis(3-phenylimidazo[1,5-a]pyridine) | |
| Compound 18: 1,1'-(1-ethyl-1H-pyrrole-2,5-diyl)bis(3-phenylimidazo[1,5-a]pyridine) | |
| Compound 19: 1,1'-(1-phenyl-1H-pyrrole-2,5-diyl)bis(3-phenylimidazo[1,5-a]pyridine) | |

TABLE 1-continued

Examples of novel imidizo derivatives

| Description | Imidizo Derivative Structure |
| --- | --- |
| Compound 20: 1,1'-(1-ethyl-1H-pyrrole-2,5-diyl)bis(3-(pyrimidin-2-yl)imidazo[1,5-a]pyridine) | |
| Compound 21: 1,1'-(1-phenyl-1H-pyrrole-2,5-diyl)bis(3-(pyrimidin-2-yl)imidazo[1,5-a]pyridine) | |
| Compound 22: 1,3,5-tris(3-phenylimidazo[1,5-a]pyridin-1-yl)benzene | |
| Compound 23: 1,3,5-tris(3-(pyridin-2-yl)imidazo[1,5-a]pyridin-1-yl)benzene | |

TABLE 1-continued

Examples of novel imidizo derivatives

| Description | Imidizo Derivative Structure |
|---|---|
| Compound 24: 1,3,5-tris(3-(pyrimidin-2-yl)imidazo[1,5-a]pyridin-1-yl)benzene | |
| Compound 25: 2,4,6-tris(3-phenylimidazo[1,5-a]pyridin-1-yl)-1,3,5-triazine | |
| Compound 26: 2,4,6-tris(3-(pyridin-2-yl)imidazo[1,5-a]pyridin-1-yl)-1,3,5-triazine | |

TABLE 1-continued

Examples of novel imidizo derivatives

| Description | Imidizo Derivative Structure |
| --- | --- |
| Compound 27: 2,4,6-tris(3-(pyrimidin-2-yl)imidazo[1,5-a]pyridin-1-yl)-1,3,5-triazine | |
| Compound 28: 2,5,8,11-tetrakis(3-phenylimidazo[1,5-a]pyridin-1-yl)perylene | |

TABLE 1-continued

Examples of novel imidizo derivatives

| Description | Imidizo Derivative Structure |
| --- | --- |
| Compound 29: 2,5,8,11-tetrakis(3-(pyridin-2-yl)imidazo[1,5-a]pyridin-1-yl)perylene | |
| Compound 30: 2,5,8,11-tetrakis(3-(pyrimidin-2-yl)imidazo[1,5-a]pyridin-1-yl)perylene | |
| Compound 31: 1,6-bis(3-phenylimidazo[1,5-a]pyridin-1-yl)anthra[1,9-bc:5,10-b'c']dithiophene | |

TABLE 1-continued

Examples of novel imidizo derivatives

| Description | Imidizo Derivative Structure |
|---|---|
| Compound 32: 1,6-bis(3-(pyridin-2-yl)imidazo[1,5-a]pyridin-1-yl)anthra[1,9-bc:5,10-b'c']dithiophene | 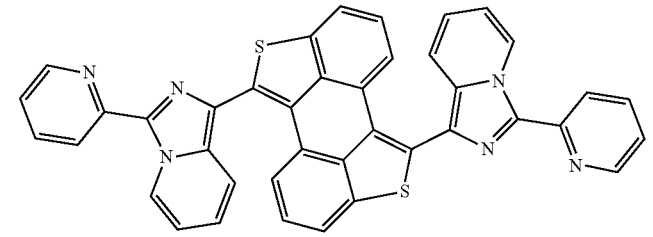 [SMILES: c1ccc(-c2nc(-c3sc4cccc5c6c(-c7nc(-c8ccccn8)n8ccccc78)sc7cccc(c3c45)c76)c3ccccn23)nc1] |
| Compound 33: 1,1'-(9,9-bis(2-ethylhexyl)-9H-fluorene-2,7-diyl)bis(3-phenylimidazo[1,5-a]pyridine) | 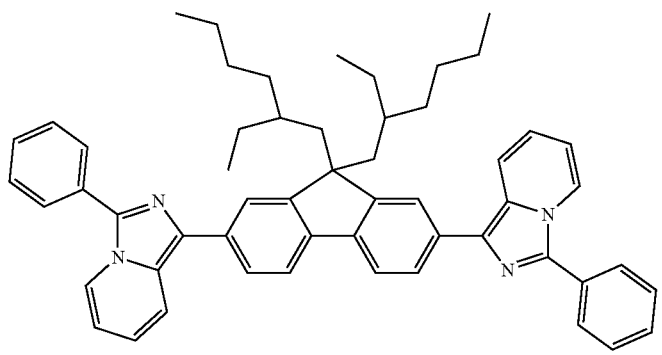 [SMILES: CCCCC(CC)CC1(CC(CC)CCCC)c2cc(-c3nc(-c4ccccc4)n4ccccc34)ccc2-c2ccc(-c3nc(-c4ccccc4)n4ccccc34)cc21] |
| Compound 34: 1,1'-(9,9-bis(2-ethylhexyl)-9H-fluorene-2,7-diyl)bis(3-(pyridin-2-yl)imidazo[1,5-a]pyridine) | 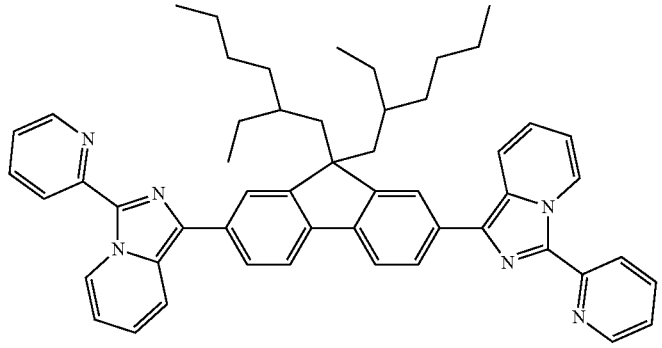 [SMILES: CCCCC(CC)CC1(CC(CC)CCCC)c2cc(-c3nc(-c4ccccn4)n4ccccc34)ccc2-c2ccc(-c3nc(-c4ccccn4)n4ccccc34)cc21] |
| Compound 35: 1,1'-(9,9-bis(2-ethylhexyl)-9H-fluorene-2,7-diyl)bis(3-(pyrimidin-2-yl)imidazo[1,5-a]pyridine) | 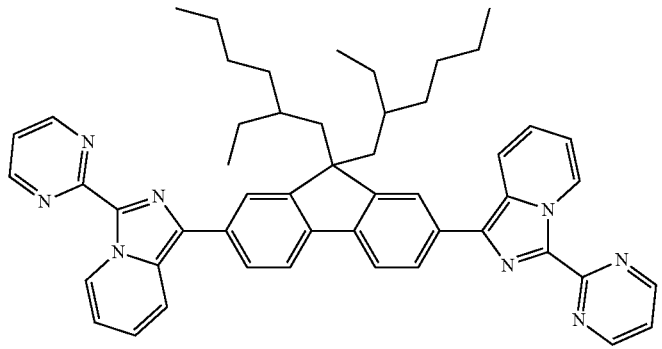 [SMILES: CCCCC(CC)CC1(CC(CC)CCCC)c2cc(-c3nc(-c4ncccn4)n4ccccc34)ccc2-c2ccc(-c3nc(-c4ncccn4)n4ccccc34)cc21] |

Representative examples of novel imidizo derivatives formed in accordance with some embodiments of the present invention listed above, but not limited thereto, are useful in many organoelectronic devices, for example in multi-layer organic light emitting devices (OLED) for display, solid lighting and other applications.

Figure 2:
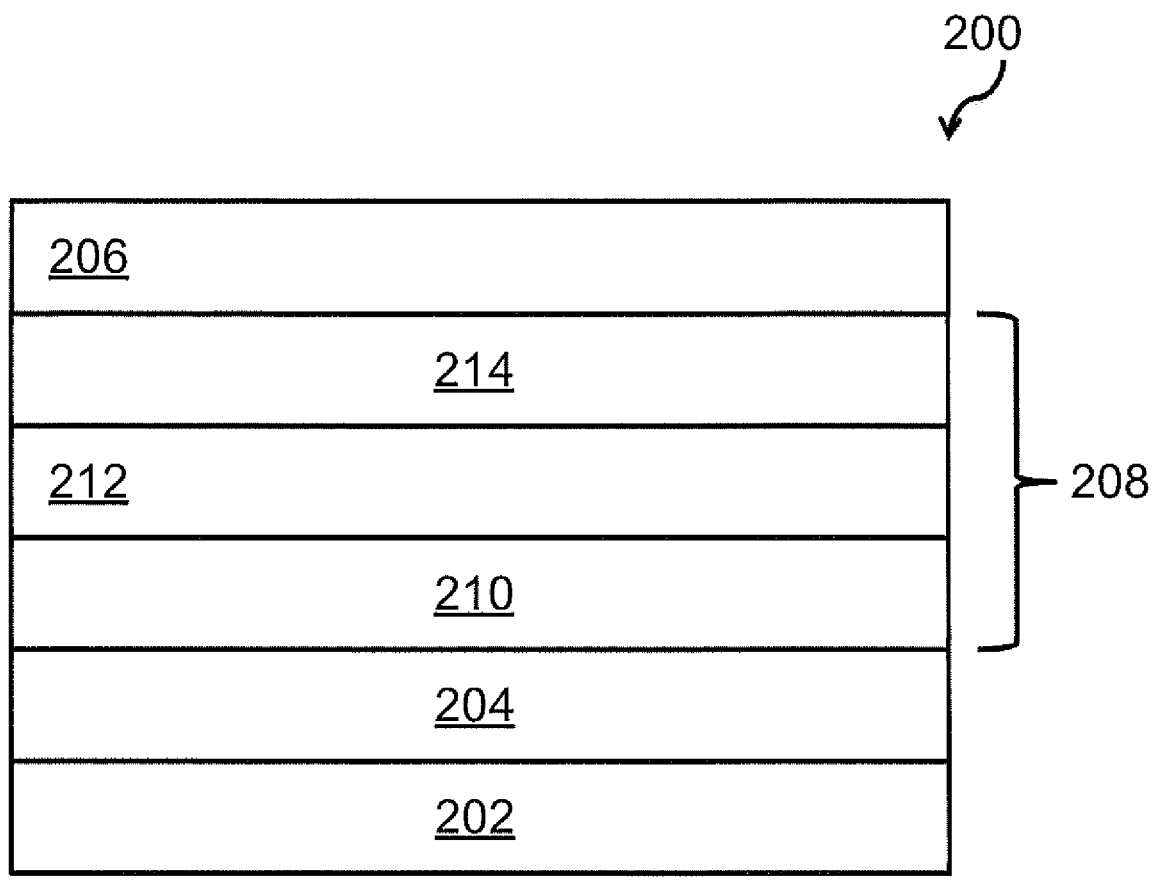
FIG. 2 depicts an organic electroluminescent device in accordance with some embodiments of the present invention.
Figure 3:
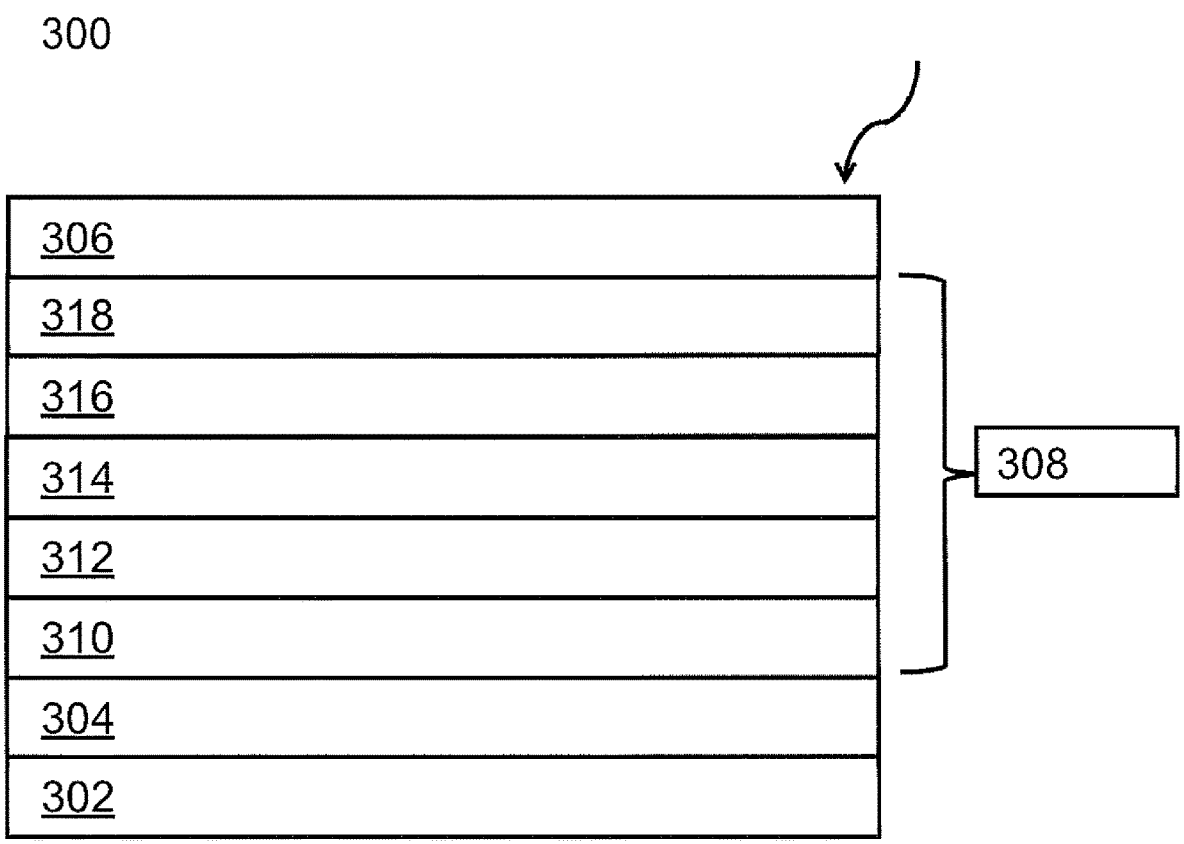
FIG. 3 depicts an organic electroluminescent device in accordance with some embodiments of the present invention.
Figure 4:
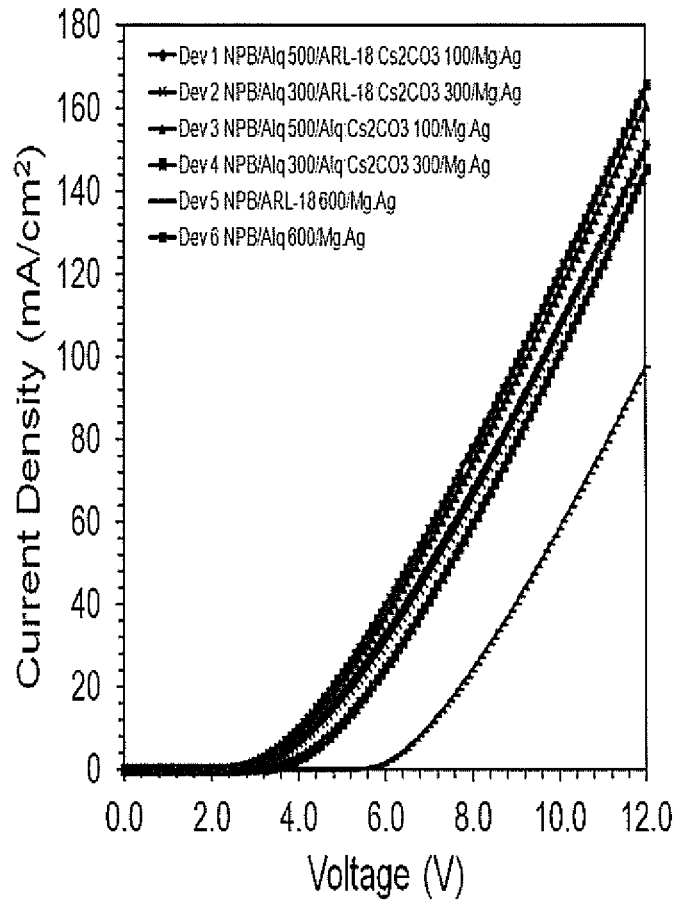
FIG. 4 depicts an efficacy plot of deviations one through six.

The typical structural schematic diagrams of the multi-layer structures of preferred organic light emitting devices that can employ this invention are detailed in FIG. 1, FIG. 2 and FIG. 3.

An OLED device 100 that uses a compound according to the invention is schematically illustrated in FIG. 1. The support layer 102 is an electrically insulating layer and can be composed of optically transparent or opaque material, such as glass or plastic. Anode 104 is separated from cathode 106 by an organic EL medium 108. The organic EL medium 108 consists of two superimposed layers 110, 112 of organic thin films. Layer 110 located on the anode 104 forms a hole-transport layer of the organic EL medium. Layer 112, located above the hole-transport layer 110, forms an electron-transport layer of the organic EL medium. In some embodiments, the cathode layer 106 can be opaque or transparent. The anode 104 and the cathode 106 are connected to an external AC or DC power source 114 by conductors 116 and 118, respectively. The power source 114 can be pulsed, periodic, or continuous.

In operation, the EL device 100 can be viewed as a diode which is forward biased when the anode 104 is at a higher potential then the cathode 106. Under these conditions, holes (positive charge carriers) are injected from the anode 104 into the hole-transport layer 110, and electrons are injected into the electron-transport layer 112. The injected holes and electrons each migrate toward the oppositely charged electrode, as shown by the arrows 120 and 122, respectively. This results in hole-electron recombination and a release of energy in part as light, thus producing electroluminescence.

The region where the hole and electron recombine is known as the recombination zone. The two-layer device structure is designed specifically to confine the recombination at the vicinity near the interface between the hole-transport layer 110 and the electron-transport layer 112 where the probability for producing electroluminescence is the highest. This recombination confinement scheme has been disclosed by Tang and Van Slyke in Applied Physics Letters, Volume 51, Page 913, 1987 and is done by choosing carrier injecting electrodes of suitable work-functions and transport materials of proper carrier mobility. Away from this interface between the organic layers, and in particular at or near the injecting electrodes, the recombination of hole and electron would generally be much less radiative due to the effect of radiative quenching by a conducting surface. In U.S. Pat. No. 7,985,974, H. Nowatari, et. al. disclosed a light emitting element comprising: an anode; a first EL layer over the anode; a first layer over the first EL layer; a second layer over and in contact with the first layer; a region including a material having a hole-transporting property and an acceptor material, the region being over and in contact with the second layer; a second EL layer over the region; and a cathode over the second EL layer, wherein the first layer includes at least one selected from the group consisting of an alkali metal, an alkaline earth metal, a rare earth metal, an alkali metal compound, an alkaline earth metal compound, and a rare earth metal compound, and wherein the second layer includes a material having an electron-transporting property.

Organic EL device 200 shown in FIG. 2 is illustrative of another EL device which can use the compound of the present invention. Support layer 202 is an electrically insulating layer and composed of optically transparent material. The anode 204 is separated from the cathode 206 by an EL medium 208, which consists of three superimposed layers 210, 212, 214 of organic thin films. Layer 210, disposed adjacent to anode 204, is the hole-transport layer. Layer 214, disposed adjacent to cathode 206, is the electron-transport layer. Layer 212, disposed in between the hole-transport layer 210 and the electron transport layer 214 is the luminescent layer. This luminescent layer 212 also serves as the recombination zone layer, where the hole and electron recombines.

The configurations of devices 100 and 200 are similar, except that an additional luminescent layer 212 is introduced in device 200 to function primarily as the site for hole-electron recombination and thus electroluminescence. In this respect, the functions of the individual organic layers are distinct and can therefore be optimized independently. Thus, the luminescent (or recombination) layer 212 can be chosen to have a desirable EL color as well as a high luminance efficiency. Likewise, the electron transport layer 214 and hole transport layer 210 can be optimized primarily for the carrier transport property.

Organic device 300, shown in FIG. 3, is illustrative of yet another EL device which can use the compound of the present invention. Support layer 302 is an electrically insulating layer and composed of optically transparent material. The anode 304 is separated from the cathode 306 by an EL medium 308, which consists of five superimposed layers 310, 312, 314, 316, 318 of organic thin films. Located on top of the anode layer 304 are, in sequence, the hole-injection layer 310, the hole-transport layer 312, the luminescent layer 314, the electron-transport layer 316, and the electron-injection layer 318. The structure of device 300 is similar to device 200, except that a hole-injection layer 310 and an electron injection layer 318 are added to improve the injection efficiency of the respective anode 304 and cathode 306. It is understood that an EL device may be constructed having either the hole injection layer 310 or electron injection layer 316 present in the organic EL medium 308 without unduly compromising the device performance.

The present invention is particular useful for forming an electron transport layer 214 or 316, and an electron injection layer 318. As an example, the present invention can be combined with alkaline metals or alkaline metal compounds to enhance the electron injection and electron transport properties of the EL device.

In one specific embodiment, 1,3-bis(3-phenylimidazo [1,5-a]pyridine-1-yl) benzene, depicted as Compound 7 in Table 1 above, is synthesized via the following general formula:

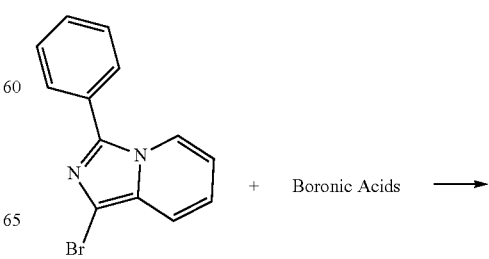

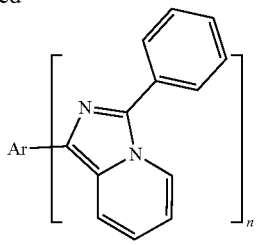

The synthesis of 1,3-bis(3-phenylimidazo [1,5-a]pyridine-1-yl) benzene is accomplished via the above formula by mixing 1 mmol equivalent of 1,3-phenylenediboronic acid, with a boronic acid such as 2.2 mmol equivalent of 1-bromo-3 phenylimidazo[1,5-1] pyridine charged with 90 ml of toluene, 15 ml of ethanol, and 15 ml of 2 N potassium carbonate. The mixed solvents are bubbled with nitrogen for 5 minutes and 0.1 g of Pd(PPh$_3$)$_4$ is added to the reaction mixture under nitrogen. The reaction mixture is then heated to reflux with efficient stirring under nitrogen protection. After the reaction proceeds for about 3 hours, 50 mg of Pd(PPh$_3$)$_4$ is added to the reaction mixture under nitrogen. The reaction mixture is allowed to reflux. To this reaction mixture, 50 ml of toluene and 20 ml of brine is added. The organic phase is separated from the reaction mixture while hot and dried with anhydrous magnesium sulfate. Solvent is removed from the reaction mixture via a vacuum rotary evaporator. 10 ml of toluene is then added to the residue. After the reaction mixture is cooled, the precipitates are filtered and washed with acetone resulting in 2.8 g of pure 3-bis(3-phenylimidazo [1,5-a]pyridine-1-yl) benzene.

In some embodiments, the reaction process described above is also used to form other imidizo derivatives. Table 2 below shows examples of imidizo derivative compounds listed in Table 1 that may be formed by the reaction of 1,3-phenylenediboronic acid with the listed boronic acid.

TABLE 2

Imidizo derivative compounds formed by the reaction of 1,3-phenylenediboronic acid and boronic acid

| Examples | Boronic Acid Structure | Imidizo Derivative Structure |
| --- | --- | --- |
| Example 1 | (3,3'-diboronic acid benzene structure) | Compound 7 |
| Example 2 | (1,4-diboronic acid benzene structure) | Compound 1 |

TABLE 2-continued

Imidizo derivative compounds formed by the reaction of 1,3-phenylenediboronic acid and boronic acid

| Examples | Boronic Acid Structure | Imidizo Derivative Structure |
|---|---|---|
| Example 3 | | Compound 22 |
| Example 4 | | Compound 10 |
| Example 5 | | Compound 33 |

In some embodiments, the imidizo derivatives formed in accordance with some embodiments of the present invention may advantageously be used in organic electronic devices, such as multi-layer organic electroluminescent (EL) devices or organic photovoltaic (OPV) devices. Organic electroluminescent devices are a class of opto-electronic devices where light emission is produced in response to an electrical current through the device.

The following examples 1-6 illustrate formation of an organic EL device 300 where the EL medium contains an invented electron injection layer material doped with cesium carbonate as an example of an alkaline metal compound.

In example 1, the EL device labeled Dev 1 in Table 3 below was fabricated with the invented material of compound 7, shown in Table 1 above, as follows: (a) An indium-tin-oxide (ITO) coated glass substrate was sequentially ultrasonicated in a commercial detergent, rinsed in deionized water, and exposed to RF-plasma in an oxygen atmosphere; (b) Onto the ITO layer was deposited N,N'-bis-(1-naphthyl)-N,N'-diphenylbenzidine (NPB) with a thickness of 750 Å, by evaporation from a tantalum boat; (c) 8-hydroxyquinoline aluminum (Alq) with thickness of 500 Å was fabricated onto the NPB layer; (d) The invented material compound 7 was then deposited with a co-deposition of 7% cesium carbonate ($Cs_2CO_3$) by atomic weight onto the Alq layer at a thickness of 100 Å; (e) A cathode layer with a thickness of 2000 Å was then deposited with a 10:1 atomic ratio of magnesium (Mg) and silver (Ag). The above sequence completes the formation of the EL device, Dev 1. The device was then hermetically packaged in a dry glove box for protection against the ambient environment.

In example 2, the EL device labeled Dev 2 in Table 3 below was fabricated with 8-hydroxyquinoline aluminum (Alq) as a comparison to Dev 1. The EL device labeled Dev 2 was fabricated as follows: (a) An indium-tin-oxide (ITO) coated glass substrate was sequentially ultrasonicated in a commercial detergent, rinsed in deionized water, and exposed to RF-plasma in an oxygen atmosphere; (b) Onto the ITO layer was deposited N,N'-bis-(1-naphthyl)-N,N'-diphenylbenzidine (NPB) with a thickness of 750 Å, by evaporation from a tantalum boat; (c) 8-hydroxyquinoline aluminum (Alq) with a thickness of 500 Å was fabricated onto the NPB layer; (d) 8-hydroxyquinoline aluminum (Alq) was then deposited with a co-deposition of 7% cesium carbonate ($Cs_2CO_3$) by atomic weight onto the previous Alq layer at a thickness of 100 Å; (e) A cathode with a thickness of 2000 Å was then deposited with a 10:1 atomic ratio of magnesium (Mg) and silver (Ag). The above sequence completes the formation of the EL device, Dev 2. The device was then hermetically packaged in a dry glove box for protection against the ambient environment.

In example 3, the EL device labeled Dev 3 in Table 3 below was fabricated with the invented material compound 7 as follows: (a) An indium-tin-oxide (ITO) coated glass substrate was sequentially ultrasonicated in a commercial detergent, rinsed in deionized water, and exposed to RF-plasma in an oxygen atmosphere; (b) Onto the ITO layer was deposited N,N'-bis-(1-naphthyl)-N,N'-diphenylbenzidine (NPB) with a thickness of 750 Å, by evaporation from a tantalum boat; (c) 8-hydroxyquinoline aluminum (Alq) with thickness of 300 Å was fabricated onto the NPB layer; (d) The invented material compound 7 was then deposited with a co-deposition of 7% cesium carbonate ($Cs_2CO_3$) by atomic weight at a thickness of 300 Å; (e) A cathode layer with a thickness of 2000 Å was then deposited with a 10:1 atomic ratio of magnesium (Mg) and silver (Ag). The above sequence completes the formation of the EL device, Dev 3. The device was then hermetically packaged in a dry glove box for protection against ambient environment.

In example 4, the EL device labeled Dev 4 in Table 3 below was fabricated with hydroxyquinoline aluminum (Alq) as a comparison to Dev 1. The EL device labeled Dev 4 was fabricated as follows: (a) An indium-tin-oxide (ITO) coated glass substrate was sequentially ultrasonicated in a commercial detergent, rinsed in deionized water, and exposed to RF-plasma in oxygen atmosphere; (b) Onto the ITO layer was deposited N,N'-bis-(1-naphthyl)-N,N'-diphenylbenzidine (NPB) with a thickness of 750 Å, by evaporation from a tantalum boat; (c) A luminescent layer of 8-hydroxyquinoline aluminum (Alq) with a thickness of 300 Å was fabricated onto the NPB layer; (d) 8-hydroxyquinoline aluminum (Alq) was then deposited onto the previous Alq layer with a co-deposition of 7% cesium carbonate ($Cs_2CO_3$) by atomic weight at a thickness of 300 Å; (e) A cathode layer with a thickness of 2000 Å was then deposited with a 10:1 atomic ratio of magnesium (Mg) and silver (Ag). The above sequence completes the formation of the EL device, Dev 4. The device was then hermetically packaged in a dry glove box for protection against ambient environment In example 5, the EL device labeled Dev 5 in Table 3 below was fabricated with the invented material compound 7. The EL device labeled Dev 5 was fabricated as follows: (a) An indium-tin-oxide (ITO) coated glass substrate was sequentially ultrasonicated in a commercial detergent, rinsed in deionized water, and exposed to RF-plasma in an oxygen atmosphere; (b) Onto the ITO layer was deposited N,N'-bis-(1-naphthyl)-N,N'-diphenylbenzidine (NPB) with a thickness of 750 Å, by evaporation from a tantalum boat; (c) The invented material of compound 7 was deposited onto the NPB layer at a thickness of 600 Å; (d) A cathode layer with a thickness of 2000 Å was then deposited with a 10:1 atomic ratio of magnesium (Mg) and silver (Ag). The above sequence completes the formation of the EL device labeled Dev 5. The device was then hermetically packaged in a dry glove box for protection against ambient environment.

In example 6, the EL device labeled Dev 6 in Table 3 below was fabricated with hydroxyquinoline aluminum (Alq) as a comparison to the invented material compound 7. The EL device labeled Dev 6 was fabricated as follows: (a) An indium-tin-oxide (ITO) coated glass substrate was sequentially ultrasonicated in a commercial detergent, rinsed in deionized water, and exposed to RF-plasma in an oxygen atmosphere; (b) Onto the ITO layer was deposited N,N'-bis-(1-naphthyl)-N,N'-diphenylbenzidine (NPB) with a thickness of 750 Å, by evaporation from a tantalum boat; (c) Hydroxyquinoline aluminum (Alq) was deposited at a thickness of 600 Å; (d) A cathode layer with a thickness of 2000 Å was then deposited with a 10:1 atomic ratio of magnesium (Mg) and silver (Ag). The above sequence completes the formation of the EL device labeled Dev 6. The device was then hermetically packaged in a dry glove box for protection against ambient environment.

The experimental examples described above are summarized in Table 3 below showing the efficacy performance in cd/A as a function of current density ($mA/cm^2$) for the six fabricated example devices Dev 1-6.

TABLE 3

Organic EL Device performance

| Device label | Current Density ($mA/cm^2$) | Applied Voltage (V) | Efficacy (cd/A) | CIE (X, Y) |
|---|---|---|---|---|
| Dev 1 | 20 $mA/cm^2$ | 5.11 V | 2.29 cd/A | 0.312, 0.541 |
| Dev 2 | 20 $mA/cm^2$ | 5.27 V | 2.32 cd/A | 0.316, 0.345 |
| Dev 3 | 20 $mA/cm^2$ | 4.88 V | 2.16 cd/A | 0.309, 0.538 |
| Dev 4 | 20 $mA/cm^2$ | 4.72 V | 2.06 cd/A | 0.311, 0.538 |
| Dev 5 | 20 $mA/cm^2$ | 7.71 V | Not measurable | 0.233, 0.383 (@100 $mA/cm^2$) |
| Dev 6 | 20 $mA/cm^2$ | 5.89 V | 1.58 cd/A | 0.312, 0.537 |

The efficacy (cd/A) plot depicted in graph 1 below indicates that the invented material doped with 7% by atomic weight of cesium carbonate ($Cs_2CO_3$) provides enhanced efficacy as compared to hydroxyquinoline aluminum (Alq) doped with 7% by atomic weight of cesium carbonate ($Cs_2CO_3$). Dev 5, with the invented material compound 7 not doped with alkali metal, demonstrated weak device performance.

The device structures to evaluate the tested material are summarized in Table 4 below.

TABLE 4

Summary of the device structures (Dev 1-6) fabricated to compare the invented material and hydroxyquinoline aluminum (Alq).

| Device label | Hole Transport layer (thickness) | Electron Transport Layer (thickness) | Electron Injection layer (thickness) | Cathode (thickness) |
| --- | --- | --- | --- | --- |
| Dev 1 | NPB (750 Å) | Alq (500 Å) | Invented Material doped with 7% atomic weight Cs2CO3 (100 Å) | Mg:Ag (2000 Å) |
| Dev 2 | NPB (750 Å) | Alq (300 Å) | Invented Material doped with 7% atomic weight Cs2CO3 (300 Å) | Mg:Ag (2000 Å) |
| Dev 3 | NPB (750 Å) | Alq (500 Å) | Alq doped with 7% atomic weight Cs2CO3 (100 Å) | Mg:Ag (2000 Å) |
| Dev 4 | NPB (750 Å) | Alq (300 Å) | Alq doped with 7% atomic weight Cs2CO3 (300 Å) | Mg:Ag (2000 Å) |
| Dev 5 | NPB (750 Å) | Invented Material - not doped (600 Å) | | Mg:Ag (2000 Å) |
| Dev 6 | NPB (750 Å) | Alq - not doped (600 Å) | | Mg:Ag (2000 Å) |

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form, except where such limit is clearly defined.

While the foregoing is directed to embodiments of the present invention, other and further embodiments of the invention may be devised without departing from the basic scope thereof.

The invention claimed is:

1. A compound of the following formula:

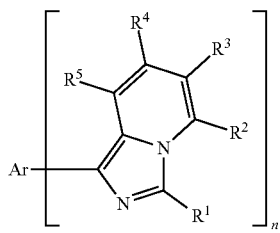

wherein, $R^1$, $R^2$, $R^3$, $R^4$, and $R^5$ are each independently a hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group;
wherein n is an integer from 2 to 4; and
wherein Ar is a linkage unit comprising aryl or heteroaryl or substituted aryl or heteroaryl groups.

2. The compound of claim 1, wherein $R^1$, $R^2$, $R^3$, $R^4$, and $R^5$ are linked to form one of a saturated ring, unsaturated ring, aromatic ring, non-aromatic ring, or heteroaromatic ring.

3. The compound of claim 1, wherein the compound is 1,4-bis(3-phenylimidazo[1,5-a]pyridin-1-yl)benzene.

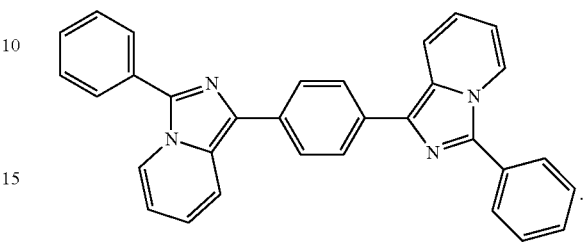

4. The compound of claim 1, wherein the compound is 1,3,5-tris(3-phenylimidazo[1,5-a]pyridin-1-yl)benzene

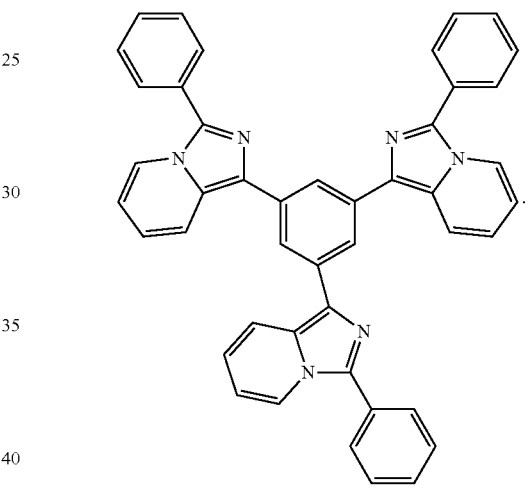

5. The compound of claim 1, wherein the compound is 1,3,5-tris(3-(pyridin-2-yl)imidazo[1,5-a]pyridin-1-yl)benzene

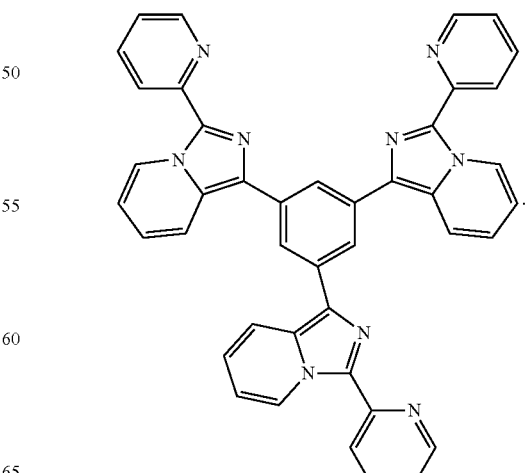

6. The compound of claim 1 wherein the compound is 2,4,6-tris(3-phenylimidazo[1,5-a]pyridin-1-yl)-1,3,5-triazine.

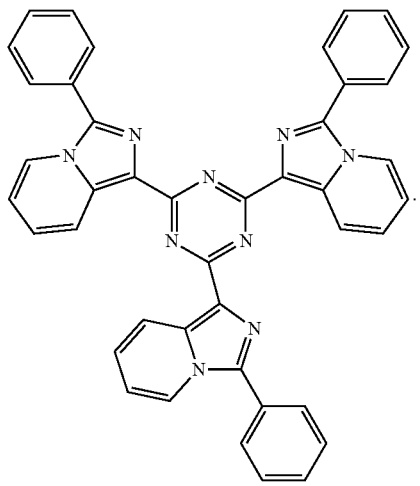 [SMILES: c1ccc(-c2nc(-c3nc(-c4nc(-c5ccccc5)n5ccccc45)nc(-c4nc(-c5ccccc5)n5ccccc45)n3)c3ccccn23)cc1]

7. The compound of claim 1, wherein n is 2.
8. The compound of claim 1, wherein n is 3.
9. The compound of claim 1, wherein n is 4.
10. The compound of claim 1, wherein the compound is 2,5-bis(3-phenylimidazo[1,5-a]pyridin-1-yl)thiophene.

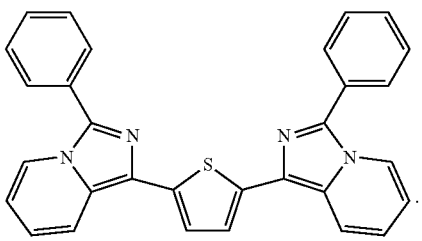 [SMILES: c1ccc(-c2nc(-c3ccc(-c4nc(-c5ccccc5)n5ccccc45)s3)c3ccccn23)cc1]

11. The method of making the compound of claim 1, formed by the following scheme:

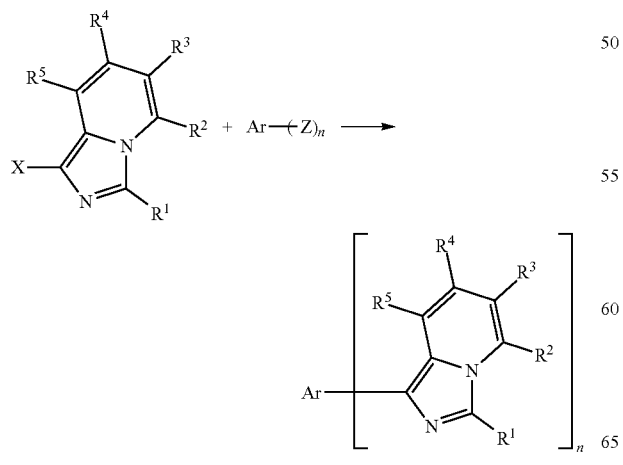

wherein, $R^1$, $R^2$, $R^3$, $R^4$, and $R^5$ are each independently hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group;

wherein X is one of chloro, bromo, iodo, or cyano;

wherein Ar is a linkage unit comprising aryl or heteroaryl groups or substituted aryl or heteroaryl groups;

wherein Z is a reactive group; and wherein n is an integer from 2 to 4.

12. The method of claim 11, wherein $R^1$, $R^2$, $R^3$, $R^4$, and $R^5$ are linked to form one of a saturated ring, unsaturated ring, aromatic ring, non-aromatic ring, or heteroaromatic ring.

13. The method of claim 11, wherein the compound is 1,4-bis(3-phenylimidazo[1,5-a]pyridin-1-yl)benzene.

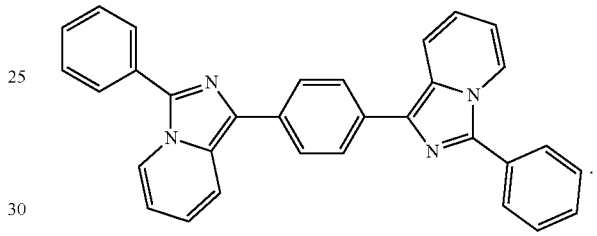

14. The method of claim 11, wherein the compound is 1,3-bis(3-phenylimidazo[1,5-a]pyridine-1-yl)benzene.

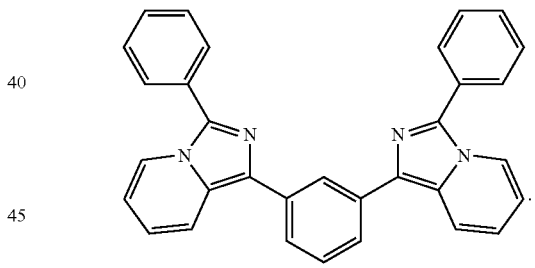

15. The method of claim 11, wherein the compound is 1,3-bis(3-(pyridin-2-yl)imidazo[1,5-a]pyridin-1-yl)benzene

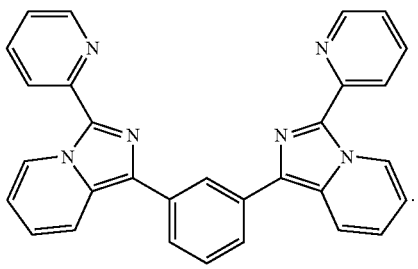 [SMILES: c1ccc(-c2nc(-c3cccc(-c4nc(-c5ccccn5)n5ccccc45)c3)c3ccccn23)nc1]

16. The method of claim 11, wherein the compound is 1,3-bis(3-(pyrimidin-2-yl)imidazo[1,5-a]pyridin-1-yl)benzene.

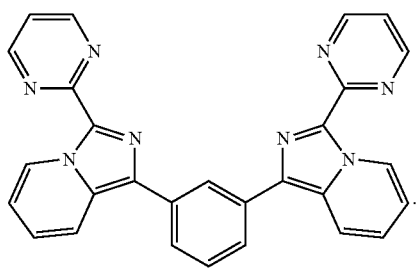 [SMILES: c1cnc(-c2nc(-c3cccc(-c4nc(-c5ncccn5)n5ccccc45)c3)c3ccccn23)nc1]

17. The method of claim 11, wherein the compound is 1,3,5-tris(3-phenylimidazo[1,5-a]pyridin-1-yl)benzene.

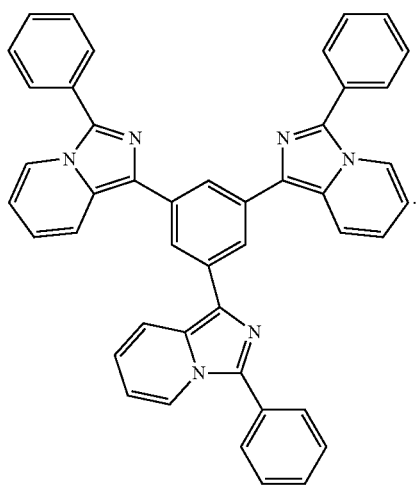 [SMILES: c1ccc(-c2nc(-c3cc(-c4nc(-c5ccccc5)n5ccccc45)cc(-c4nc(-c5ccccc5)n5ccccc45)c3)c3ccccn23)cc1]

18. The method of claim 11, wherein the compound is 1,3,5-tris(3-(pyridin-2-yl)imidazo[1,5-a]pyridin-1-yl)benzene

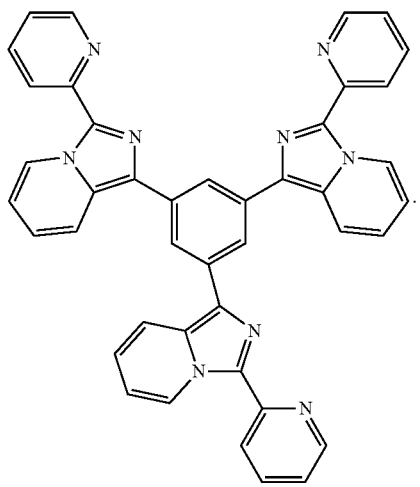 [SMILES: c1ccc(-c2nc(-c3cc(-c4nc(-c5ccccn5)n5ccccc45)cc(-c4nc(-c5ccccn5)n5ccccc45)c3)c3ccccn23)nc1]

19. The method of claim 11, wherein the compound is 2,4,6-tris(3-phenylimidazo[1,5-a]pyridin-1-yl)-1,3,5-triazine.

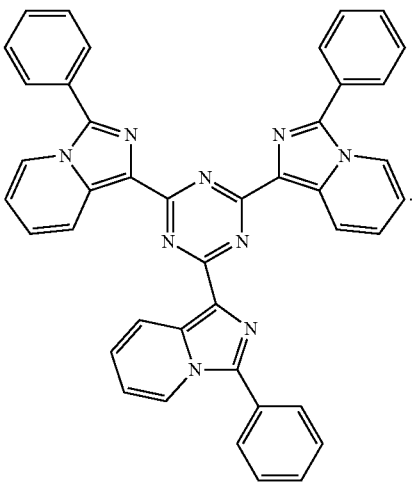 [SMILES: c1ccc(-c2nc(-c3nc(-c4nc(-c5ccccc5)n5ccccc45)nc(-c4nc(-c5ccccc5)n5ccccc45)n3)c3ccccn23)cc1]

20. The compound of claim 11, wherein the compound is 1,1'-(9,9-bis(2-ethylhexyl)-9H-fluorene-2,7-diyl)bis(3-phenylimidazo[1,5-a]pyridine)

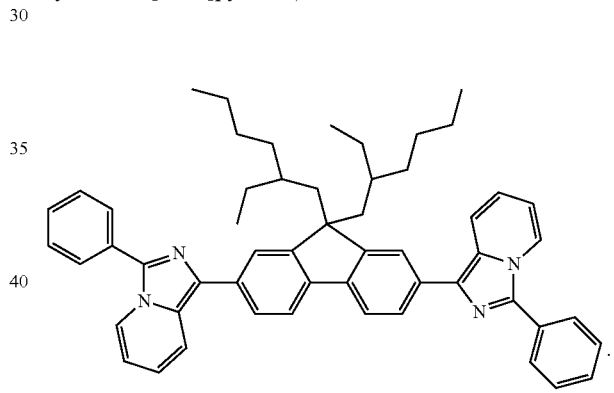

21. The method of claim 11, wherein n is 2.
22. The method of claim 11, wherein n is 3.
23. The method of claim 11, wherein n is 4.
24. The method of claim 11, wherein the compound is 2,5-bis(3-phenylimidazo[1,5-a]pyridin-1-yl)thiophene

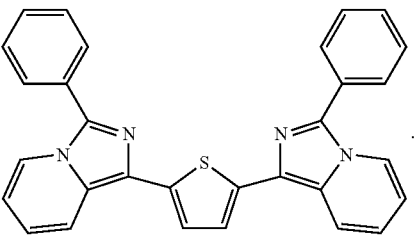 [SMILES: c1ccc(-c2nc(-c3ccc(-c4nc(-c5ccccc5)n5ccccc45)s3)c3ccccn23)cc1]

25. The method of claim 11, wherein the compound is 1,1'-(9,9-bis(2-ethylhexyl)-9H-fluorene-2,7-diyl)bis(3-phenylimidazo[1,5-a]pyridine).

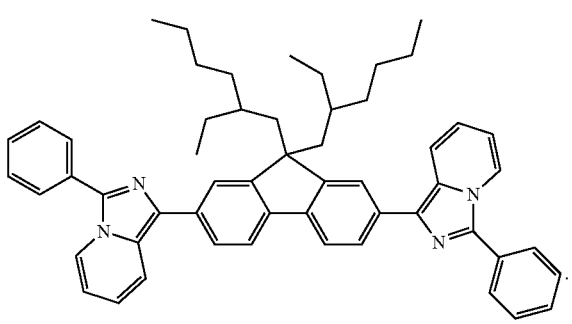 [SMILES: CCCCC(CC)CC1(CC(CC)CCCC)c2cc(-c3nc(-c4ccccc4)n4ccccc34)ccc2-c2ccc(-c3nc(-c4ccccc4)n4ccccc34)cc21]

26. An organic electroluminescence device, comprising:
a support layer;
an anode disposed atop the support layer;
a cathode disposed opposite the anode; and
an organic electroluminescence material disposed between the anode and the cathode, wherein the organic electroluminescence material comprises a compound of the following formula:

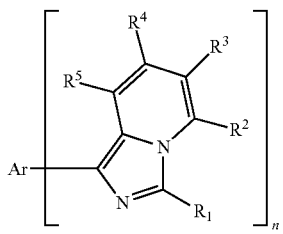

wherein, $R^1$, $R^2$, $R^3$, $R^4$, and $R^5$ are each independently a hydrogen, an alkyl, an alkenyl, an alkynyl, an alkoxyl, an amino, an alkyl-substituted amino, an aryl-substituted amino, an aryl, a heteroaryl, a cyano group, a fluoro group, a chloro group, or a bromo group; wherein n is an integer from 2 to 4; and wherein Ar is a linkage unit comprising aryl or heteroaryl or substituted aryl or heteroaryl groups.

27. The device of claim 26, wherein $R^1$, $R^2$, $R^3$, $R^4$, and $R^5$ are linked to form one of a saturated ring, unsaturated ring, aromatic ring, non-aromatic ring, or heteroaromatic ring.

28. The device of claim 26, wherein the support layer comprises one of an optically transparent material or an opaque material.

29. The device of claim 26, wherein the organic electroluminescence material further comprises a hole-transport layer disposed atop the anode and an electron-transport layer disposed atop the hole-transport layer.

30. The device of claim 29, further comprising a luminescent layer disposed between the hole-transport layer and the electron-transport layer.

31. The device of claim 26, wherein the anode and the cathode are connected to a power source.

* * * * *